(12) United States Patent
Zhang

(10) Patent No.: US 7,908,006 B2
(45) Date of Patent: Mar. 15, 2011

(54) CARDIAC PACING RESPONSE CLASSIFICATION USING AN ADAPTABLE CLASSIFICATION INTERVAL

(75) Inventor: Geng Zhang, Newbury Park, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 247 days.

(21) Appl. No.: 11/012,443

(22) Filed: Dec. 15, 2004

(65) Prior Publication Data

US 2006/0129194 A1   Jun. 15, 2006

(51) Int. Cl.
*A61N 1/08* (2006.01)
(52) U.S. Cl. .......................................................... 607/28
(58) Field of Classification Search .............. 607/28–29, 607/9
See application file for complete search history.

(56) References Cited

U.S. PATENT DOCUMENTS

| | | | |
|---|---|---|---|
| 4,505,276 A | 3/1985 | Markowitz et al. |
| 4,543,963 A | 10/1985 | Gessman |
| 4,569,350 A | 2/1986 | Mumford et al. |
| 5,000,189 A | 3/1991 | Throne et al. |
| 5,139,028 A | 8/1992 | Steinhaus et al. |
| 5,217,021 A | 6/1993 | Steinhaus et al. |
| 5,253,644 A | 10/1993 | Elmvist |
| 5,273,035 A | 12/1993 | Markowitz et al. |
| 5,312,450 A | 5/1994 | Markowitz |
| 5,350,410 A | 9/1994 | Kleks et al. |
| 5,374,280 A | 12/1994 | Den Dulk |
| 5,383,910 A | 1/1995 | den Dulk |
| 5,447,519 A | 9/1995 | Peterson |
| 5,458,623 A | 10/1995 | Lu et al. |
| 5,476,482 A | 12/1995 | Lu |
| 5,534,017 A | 7/1996 | van Krieken et al. |
| 5,549,648 A | 8/1996 | Stoop |
| 5,601,615 A | 2/1997 | Markowitz et al. |
| 5,653,738 A | 8/1997 | Sholder |
| 5,683,431 A | 11/1997 | Wang |
| 5,713,933 A | 2/1998 | Condie et al. |
| 5,766,229 A * | 6/1998 | Bornzin ......................... 607/28 |
| 5,779,645 A | 7/1998 | Olson et al. |
| 5,817,027 A | 10/1998 | Arand et al. |

(Continued)

FOREIGN PATENT DOCUMENTS

EP          1116494       7/2001

OTHER PUBLICATIONS

Office Action from U.S. Appl. No. 10/734,599 dated Sep. 21, 2009, 7 pages.

(Continued)

*Primary Examiner* — Carl H Layno
*Assistant Examiner* — Joseph Stoklosa
(74) *Attorney, Agent, or Firm* — Hollingsworth & Funk, LLC

(57) ABSTRACT

Methods and systems involve the formation of a classification interval used for sensing a cardiac signal following a pacing pulse to determine a cardiac response to pacing. One or more cardiac signals associated with a type of cardiac pacing response are sensed. The timing of at least one feature of the cardiac signal may be used to define an initial cardiac response classification interval. The classification interval is adapted based on the variability of the timing of the feature. The classification interval may be adapted using a predetermined number of additional cardiac signals or until a predetermined stability criterion is achieved.

19 Claims, 11 Drawing Sheets

U.S. PATENT DOCUMENTS

| | | | |
|---|---|---|---|
| 5,843,137 A * | 12/1998 | Condie et al. ............... 607/28 |
| 5,857,977 A | 1/1999 | Caswell et al. |
| 5,871,509 A | 2/1999 | Noren |
| 6,038,474 A | 3/2000 | Zhu et al. |
| 6,052,620 A | 4/2000 | Gillberg et al. |
| 6,076,014 A | 6/2000 | Alt |
| 6,101,416 A | 8/2000 | Sloman |
| 6,128,535 A | 10/2000 | Maarse |
| 6,163,724 A | 12/2000 | Hemming et al. |
| 6,167,307 A | 12/2000 | Hess |
| 6,175,766 B1 | 1/2001 | Bomzin et al. |
| 6,221,011 B1 | 4/2001 | Bardy |
| 6,259,950 B1 | 7/2001 | Mann et al. |
| 6,270,457 B1 | 8/2001 | Bardy |
| 6,275,731 B1 | 8/2001 | Zhu et al. |
| 6,277,072 B1 | 8/2001 | Bardy |
| 6,280,380 B1 | 8/2001 | Bardy |
| 6,312,378 B1 | 11/2001 | Bardy |
| 6,336,903 B1 | 1/2002 | Bardy |
| 6,358,203 B2 | 3/2002 | Bardy |
| 6,363,281 B1 | 3/2002 | Zhu et al. |
| 6,368,284 B1 | 4/2002 | Bardy |
| 6,389,316 B1 | 5/2002 | Bornzin et al. |
| 6,398,728 B1 | 6/2002 | Bardy |
| 6,408,210 B1 | 6/2002 | Bornzin et al. |
| 6,418,343 B1 | 7/2002 | Zhang et al. |
| 6,440,066 B1 | 8/2002 | Bardy |
| 6,449,503 B1 | 9/2002 | Hsu |
| 6,456,881 B1 | 9/2002 | Bomzin et al. |
| 6,473,649 B1 | 10/2002 | Gryzwa et al. |
| 6,496,730 B1 | 12/2002 | Kleckner et al. |
| 6,498,949 B2 | 12/2002 | Levine et al. |
| 6,505,070 B1 | 1/2003 | Backers |
| 6,505,071 B1 | 1/2003 | Zhu et al. |
| 6,609,028 B2 | 8/2003 | Struble |
| 6,611,714 B1 | 8/2003 | Mo |
| 6,625,489 B2 | 9/2003 | Sheth et al. |
| 6,643,549 B1 | 11/2003 | Bradley et al. |
| 6,684,100 B1 | 1/2004 | Sweeney et al. |
| 6,697,673 B1 | 2/2004 | Lu |
| 6,721,601 B1 | 4/2004 | Bornzin et al. |
| 6,885,893 B1 * | 4/2005 | Lu ............................. 607/28 |
| 6,925,326 B1 | 8/2005 | Levine et al. |
| 6,950,704 B1 * | 9/2005 | Bradley ...................... 607/28 |
| 7,006,869 B2 | 2/2006 | Bradley |
| 7,076,297 B2 | 7/2006 | Limousin et al. |
| 7,123,954 B2 | 10/2006 | Narayan et al. |
| 7,130,685 B2 | 10/2006 | Casavant et al. |
| 7,130,690 B2 | 10/2006 | Rueter et al. |
| 7,177,685 B2 | 2/2007 | Lincoln et al. |
| 7,324,848 B1 * | 1/2008 | Turcott ........................ 607/17 |
| 7,433,736 B2 * | 10/2008 | Rueter et al. ................ 607/28 |
| 7,477,932 B2 | 1/2009 | Lee et al. |
| 2003/0125777 A1 | 7/2003 | Ding et al. |
| 2004/0260348 A1 | 12/2004 | Bakken et al. |
| 2005/0080347 A1 | 4/2005 | Sheth et al. |
| 2005/0131476 A1 | 6/2005 | Kim et al. |
| 2005/0131477 A1 | 6/2005 | Meyer et al. |

OTHER PUBLICATIONS

Office Action from U.S. Appl. No. 11/012,430 dated Feb. 12, 2007, 10 pages.
Office Action from U.S. Appl. No. 11/012,430 dated Jun. 11, 2007, 11 pages.
Office Action from U.S. Appl. No. 11/012,430 dated Feb. 7, 2008, 12 pages.
Office Action from U.S. Appl. No. 11/012,430 dated Jan. 23, 2009, 12 pages.
Office Action from U.S. Appl. No. 11/012,430 dated Jul. 7, 2009, 8 pages.
Office Action from U.S. Appl. No. 11/012,433 dated Dec. 19, 2006, 9 pages.
Office Action from U.S. Appl. No. 11/012,433 dated Feb. 5, 2008, 12 pages.
Office Action from U.S. Appl. No. 11/012,433 dated Aug. 22, 2008, 12 pages.
Notice of Allowance from U.S. Appl. No. 11/012,709 dated Jan. 13, 2010, 12 pages.
Office Action dated Feb. 7, 2006 from U.S. Appl. No. 10/734,599, 16 pages.
Office Action Response dated Jun. 5, 2006 from U.S. Appl. No. 10/734,599, 18 pages.
Office Action dated Sep. 21, 2006 from U.S. Appl. No. 10/734,599, 8 pages.
Office Action Response dated Jan. 22, 2007 from U.S. Appl. No. 10/734,599, 14 pages.
Office Action dated Dec. 6, 2007 from U.S. Appl. No. 10/734,599, 9 pages.
Office Action Response dated Feb. 6, 2008 from U.S. Appl. No. 10/734,599, 16 pages.
Office Action dated Mar. 18, 2009 from U.S. Appl. No. 10/734,599, 10 pages.
Office Action Response dated Jun. 9, 2009 from U.S. Appl. No. 10/734,599, 14 pages.
Interview Summary dated Sep. 18, 2009 from U.S. Appl. No. 10/734,599, 2 pages.
Office Action Response dated Dec. 21, 2009 from U.S. Appl. No. 10/734,599, 14 pages.
Notice of Allowance dated Mar. 19, 2010 from U.S. Appl. No. 10/734,599, 4 pages.
Notice of Allowance dated Apr. 2, 2009 from U.S. Appl. No. 11/012,433, 6 pages.
Office Action Response dated Feb. 20, 2009 from U.S. Appl. No. 11/012,433, 11 pages.
Office Action dated Jan. 30, 2009 from U.S. Appl. No. 11/012,433, 2 pages.
Office Action Response dated Jun. 5, 2008 from U.S. Appl. No. 11/012,433, 9 pages.
Office Action Response dated Nov. 1, 2007 from U.S. Appl. No. 11/012,433, 6 pages.
Office Action dated Aug. 1, 2007 from U.S. Appl. No. 11/012,433, 6 pages.
Office Action Response dated Apr. 19, 2007 from U.S. Appl. No. 11/012,433, 10 pages.
Office Action Response dated Apr. 8, 2010 from U.S. Appl. No. 11/012,430, 8 pages.
Office Action dated Feb. 24, 2010 from U.S. Appl. No. 11/012,430, 5 pages.
Office Action Response dated Feb. 12, 2010 from U.S. Appl. No. 11/012,430, 9 pages.
Office Action dated Dec. 10, 2009 from U.S. Appl. No. 11/012,430, 10 pages.
Office Action Response dated Sep. 22, 2009 from U.S. Appl. No. 11/012,430, 11 pages.
Office Action Response dated Apr. 20, 2009 from U.S. Appl. No. 11/012,430, 8 pages.
Office Action Response dated Sep. 30, 2008 from U.S. Appl. No. 11/012,430, 15 pages.
Office Action dated Jun. 11, 2008 from U.S. Appl. No. 11/012,430, 6 pages.
Supplemental Office Action Response dated Feb. 19, 2008 from U.S. Appl. No. 11/012,430, 10 pages.
Office Action dated Oct. 17, 2007 from U.S. Appl. No. 11/012,430, 4 pages.
Office Action Response dated Sep. 11, 2007 from U.S. Appl. No. 11/012,430, 9 pages.
Office Action Response dated May 8, 2007 from U.S. Appl. No. 11/012,430, 16 pages.
Reply Brief dated May 5, 2009 from U.S. Appl. No. 11/012,692, 9 pages.
Examiner Answer dated Mar. 12, 2009 from U.S. Appl. No. 11/012,692, 12 pages.
Appeal Brief dated Dec. 8, 2008 from U.S. Appl. No. 11/012,692, 25 pages.
Office Action dated Aug. 25, 2008 from U.S. Appl. No. 11/012,692, 8 pages.
Office Action Response dated Jun. 2, 2008 from U.S. Appl. No. 11/012,692, 8 pages.

Office Action dated Dec. 3, 2007 from U.S. Appl. No. 11/012,692, 6 pages.
Office Action Response dated Sep. 26, 2007 from U.S. Appl. No. 11/012,692, 6 pages.
Office Action dated Aug. 22, 2007 from U.S. Appl. No. 11/012,692, 6 pages.
Office Action dated Nov. 29, 2006 from U.S. Appl. No. 11/012,709, 8 pages.
Office Action Response dated Feb. 28, 2007 from U.S. Appl. No. 11/012,709, 7 pages.
Office Action dated May 24, 2007 from U.S. Appl. No. 11/012,709, 7 pages.
Office Action Response dated Sep. 24, 2007 from U.S. Appl. No. 11/012,709, 6 pages.
Office Action dated Oct. 17, 2007 from U.S. Appl. No. 11/012,709, 6 pages.
Office Action Response dated Jan. 17, 2008 from U.S. Appl. No. 11/012,709, 7 pages.
Office Action dated Oct. 7, 2008 from U.S. Appl. No. 11/012,709, 5 pages.
Office Action Response dated Dec. 8, 2008 from U.S. Appl. No. 11/012,709, 6 pages.
Office Action dated Jan. 6, 2009 from U.S. Appl. No. 11/012,709, 3 pages.
Office Action dated Feb. 20, 2009 from U.S. Appl. No. 11/012,709, 4 pages.
Office Action Response dated Feb. 25, 2009 from U.S. Appl. No. 11/012,709, 7 pages.
Office Action dated Mar. 19, 2009 from U.S. Appl. No. 11/012,709, 5 pages.
Office Action Response dated Jul. 20, 2009 from U.S. Appl. No. 11/012,709, 7 pages.
Notice of Non-Compliant office action response dated Sep. 18, 2009 from U.S. Appl. No. 11/012,709, 3 pages.
Non-Compliant Response submitted Oct. 14, 2009 to office action dated Sep. 18, 2009 from U.S. Appl. No. 11/012,709, 6 pages.
Notice of Allowance dated Sep. 13, 2007 from U.S. Appl. No. 11/012,608, 7 pages.
Office Action Response dated Jun. 11, 2007 from U.S. Appl. No. 11/012,608, 10 pages.
Office Action dated Mar. 7, 2007 from U.S. Appl. No. 11/012,608, 7 pages.
International Preliminary Report on Patentability dated Jun. 28, 2007 from PCT Application No. PCT/US2005/044816, 12 pages.
International Search Report and Written Opinion dated Aug. 30, 2006 from PCT Application No. PCT/US2005/044816, 20 pages.
Office Action dated Feb. 5, 2008 from U.S. Appl. No. 11/012,433, 12 pages.
Office Action Response submitted Jun. 6, 2008 to office action dated Feb. 5, 2008 from U.S. Appl. No. 11/012,433, 9 pages.
Office Action Response submitted Apr. 19, 2007 to office action dated Dec. 19, 2006 from U.S. Appl. No. 11/012,433, 10 pages.
Office Action Response submitted Nov. 1, 2007 to office action dated Aug. 1, 2007 from U.S. Appl. No. 11/012,433, 6 pages.
Notice of Allowance dated Dec. 13, 2010 from U.S. Appl. No. 11/012,430, 15 pages.

* cited by examiner

CARDIAC PACING RESPONSE CLASSIFICATION USING AN ADAPTABLE CLASSIFICATION INTERVAL

RELATED PATENT DOCUMENT

This patent application is related to commonly owned U.S. patent application Ser. No. 11/012,709, filed Dec. 15, 2004, which is incorporated herein by reference.

FIELD OF THE INVENTION

The present invention relates generally to implantable medical devices and, more particularly, to classifying a cardiac response following delivery of a pace pulse.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac pacemaker/defibrillators, have been used as an effective treatment for patients with serious arrhythmias. These systems typically comprise circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal following the contraction is denoted the captured response (CR). The captured response may include an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Capture detection allows the cardiac rhythm management system to adjust the energy level of pace pulses to correspond to the optimum energy expenditure that reliably produces a contraction. Further, capture detection allows the cardiac rhythm management system to initiate a back-up pulse at a higher energy level whenever a pace pulse does not produce a contraction.

At times, a pacing pulse may merge with an intrinsic beat, producing a fusion beat. A fusion beat is a cardiac contraction that occurs when two cardiac depolarizations of a particular chamber, but from separate initiation sites, merge. When the heart is being paced, a fusion beat may occur when an intrinsic cardiac depolarization of a particular chamber merges with a pacemaker output pulse within that chamber. Fusion beats, as seen on electrocardiographic recordings, exhibit various morphologies. The merging depolarizations of a fusion beat do not contribute evenly to the total depolarization.

Pseudofusion occurs when a pacemaker output pulse is superimposed upon a spontaneous P wave during atrial pacing or upon a spontaneous QRS complex during ventricular pacing. In pseudofusion, the pacing stimulus may be ineffective because the tissue around the electrode has already spontaneously depolarized and is in its refractory period.

During normal pacing, the presence of fusion or pseudofusion beats may be of little consequence except for wasted energy due to the generation of unnecessary pace pulses. However, detection of fusion or pseudofusion beats may be required during an automatic capture or threshold determination procedures. Fusion or pseudofusion beats may cause false detection of capture and may lead to erroneous capture threshold values.

SUMMARY OF THE INVENTION

The present invention involves various methods and devices for classifying cardiac responses to pacing stimulation. One embodiment of the invention is directed to a method of forming a classification interval used for sensing a cardiac signal following a pacing pulse to determine a cardiac response to pacing. One or more cardiac signals associated with a type of cardiac pacing response are sensed. The variability of the timing of one or more features of the cardiac signals are determined. A cardiac response classification interval is formed using the timing variability.

Another embodiment of the invention is directed to a medical system that may be initialized for detecting cardiac responses to pacing. The medical system includes a pacing circuit configured to deliver pacing pulses to a heart chamber. A sensing circuit is configured to sense cardiac signals associated with the pacing pulses. The medical system includes a processor coupled to the sensing circuit. The processor is configured to determine a cardiac response classification interval based on a timing variability of a feature of cardiac signals associated with a type of cardiac pacing response. The cardiac response classification interval defines a period of time after a pacing pulse that a cardiac signal is sensed to determine a response to a pacing pulse.

The above summary of the present invention is not intended to describe each embodiment or every implementation of the present invention. Advantages and attainments, together with a more complete understanding of the invention, will become apparent and appreciated by referring to the

Figure 1A:
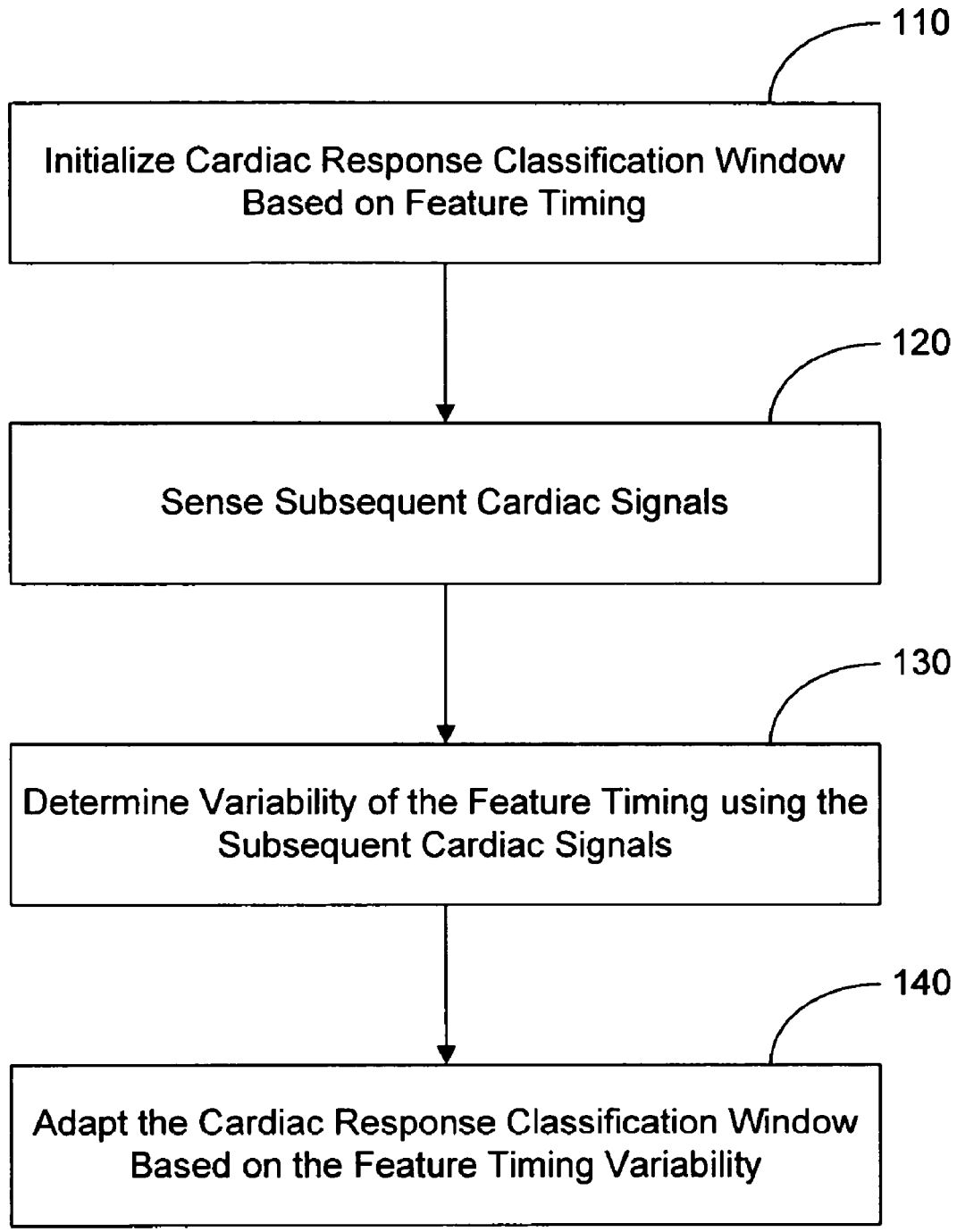
FIG. 1A is a flowchart illustrating a method of forming a cardiac response classification interval in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

After delivery of a pacing pulse to a heart chamber, various cardiac responses to the pacing pulse are possible. In one scenario, the pacing pulse may generate a propagating wavefront of depolarization resulting in a contraction of the heart chamber. In this scenario, the pacing pulse is said to have captured the heart chamber. Capture of the heart chamber may occur if the pacing pulse has sufficient energy and is delivered during a non-refractory period. If the pacing pulse does not produce contraction of the chamber, the cardiac response is referred to as non-capture or loss of capture. Non-capture may occur, for example, if the pacing pulse energy is too low, and/or if the pacing pulse is delivered during a refractory period of the cardiac tissue. In another scenario, an intrinsic depolarization wavefront may merge with a depolarization wavefront produced by the pacing pulse. The merged intrinsic and paced beats are referred to as a fusion beat.

The minimum pacing energy that produces capture is referred to as the capture threshold. It is desirable for a pace pulse to have sufficient energy to capture the heart without expending excess energy above the capture threshold. Thus, accurate determination of the capture threshold is desirable for efficient pacing.

Embodiments of the invention involve methodologies used for capture detection. The methods and systems described herein advantageously utilize the stable morphology of the captured response signal to discriminate between capture and fusion beats. The variability in the timing of a particular feature of a captured response signal may be determined with some degree of confidence. The timing variability of a captured response signal feature may be used in connection with capture verification as exemplified in the embodiments described below.

Capture of a heart chamber may be detected by analyzing the cardiac signal of the heart chamber following a pacing pulse. The cardiac signal is sensed during a classification interval initiated after a blanking period that follows the pacing pulse. The cardiac signal sensed within the classification interval is used to determine the cardiac response to the pacing pulse. For example, one or more features, samples, or morphological characteristics of the cardiac signal sensed within the classification interval may be compared to a template or other criteria characterizing a particular type of cardiac response to pacing. For example, the template may characterize a captured response, a non-captured response, or a fusion beat. If the cardiac signal sensed during the classification interval is consistent with the template, then the cardiac response to the pacing pulse is classified as the particular type of pacing response represented by the template.

A cardiac signal may be considered to be consistent with a template if the features, samples, or morphological characteristics of the cardiac signal are determined to be sufficiently similar to the template features, samples, or morphological characteristics. If a cardiac signal is sufficiently similar to a template representative of a particular type of cardiac response, then the cardiac signal may be classified as the particular type of cardiac response.

Some embodiments are directed to methods and systems for implementing an adaptable cardiac response classification interval useful for classifying a cardiac response to a pacing pulse. The classification interval may be adapted, for example, using statistical parameters associated with one or more features of the cardiac response signal. The adaptable classification interval may be utilized to detect capture and/or to discriminate between a captured response and a fusion beat.

The adaptable classification interval represents the period of time following a pacing pulse that a cardiac signal feature indicative of a particular type of cardiac pacing response, e.g., capture, is most likely to be detected. The cardiac signal sensed during the adaptable interval is used to determine the cardiac pacing response. An adaptable classification interval may be individualized for each patient, thereby reducing cross patient variance. The adaptable classification interval may be particularly useful in discriminating between fusion and capture for atrial pacing because atrial fusion management cannot rely on shortening the AV delay to enforce pacing and avoid fusion as in ventricular fusion management.

A method of initializing and adapting a cardiac response classification interval is illustrated in the flowchart of FIG. 1A. The classification interval comprises a period of time during which a particular feature of the cardiac signal is most likely to be detected for a particular type of cardiac pacing response. The classification interval may be initialized 110 based on the timing of a cardiac signal feature, such as a cardiac signal feature associated with a captured response. The cardiac signal feature may comprise, for example, a positive peak, negative peak, or other morphological characteristic of the cardiac signal.

The duration of the initial classification interval may have a predetermined length. In some embodiments, the timing of the cardiac signal feature may be used to define the central point of the classification interval. In other embodiments, the classification interval may be otherwise temporally oriented with respect to the cardiac signal feature.

In one scenario, the timing of the feature used for the initial classification interval is determined based on a cardiac response template generated during a template initialization procedure. The template initialization procedure may be performed to acquire a template comprising one or more features that characterize a captured response.

Following initialization of the classification interval, one or more subsequent cardiac signals associated with the type of cardiac response, e.g., a captured response, are sensed 120. The one or more subsequent cardiac signals may be sensed, for example, following pacing pulses delivered in connection with the patient's prescribed pacing regimen, or during other processes involving cardiac pacing and capture detection. The timing variability of the cardiac signal feature is determined 130 using historic and/or the subsequent cardiac signals. The duration of the classification interval is adapted 140 based on the timing variability.

Figure 1B:
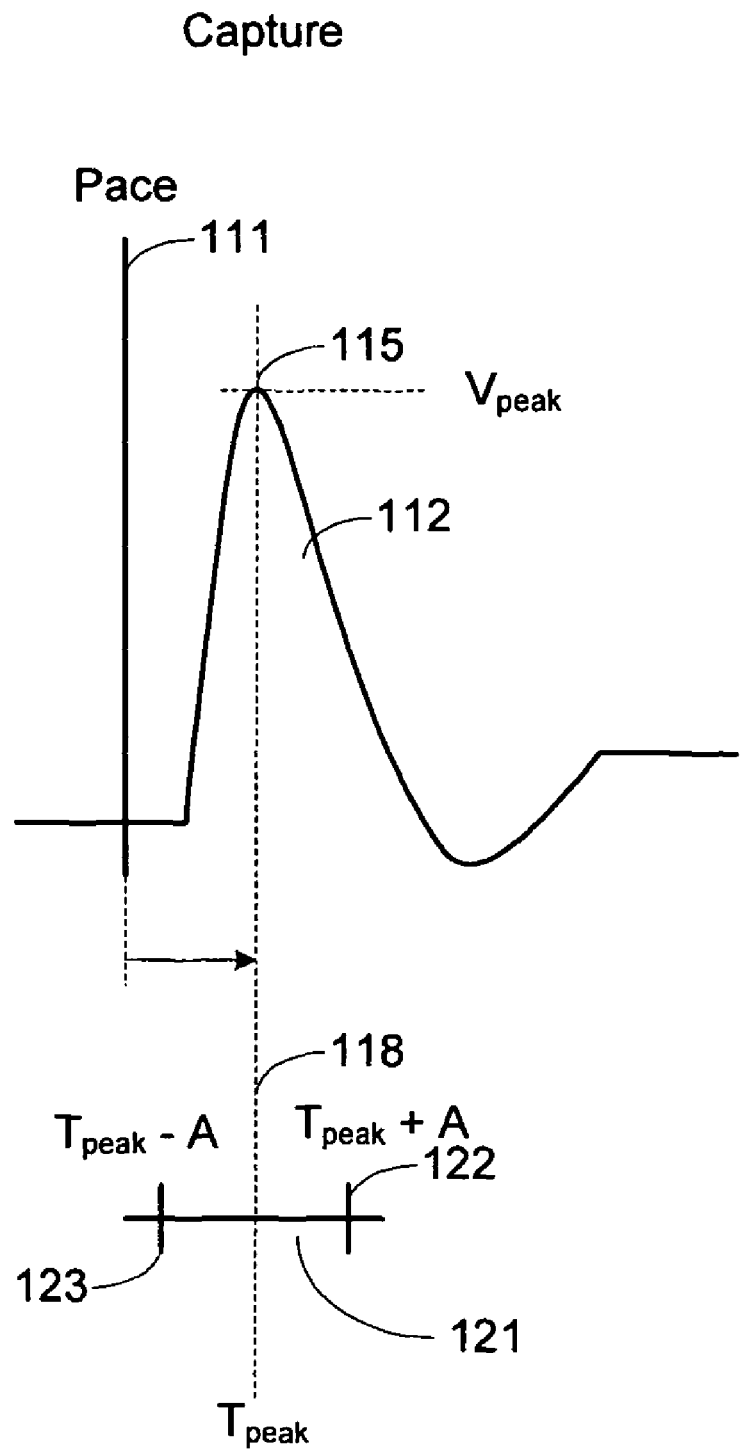
FIG. 1B is a graph illustrating a classification response interval oriented with respect to a feature of a captured response signal in accordance with embodiments of the invention.

FIG. 1B graphically illustrates the orientation of the classification interval with respect to a selected cardiac signal feature, which in this example comprises the positive peak of the cardiac signal. In this embodiment, the classification interval 121 of duration 2×A is initialized based on the timing 118 of the peak 115 of a captured response signal 112 that follows a pacing pulse 111, as illustrated by the graph of FIG. 1B. The peak timing 118 marks the center of the classification interval 121.

Following initialization, one or more paces subsequent to pace 111 are delivered and the system senses the cardiac signals following delivery of the subsequent paces. If the subsequent signals indicate capture, then the peak amplitude timing of each of the subsequent captured response signals is detected. The variability of the peak amplitude timing of the captured response signals is determined. The peak amplitude timing variability is used to update or adapt the upper and lower bounds 122, 123 of the initial classification interval 121.

Figure 2A:
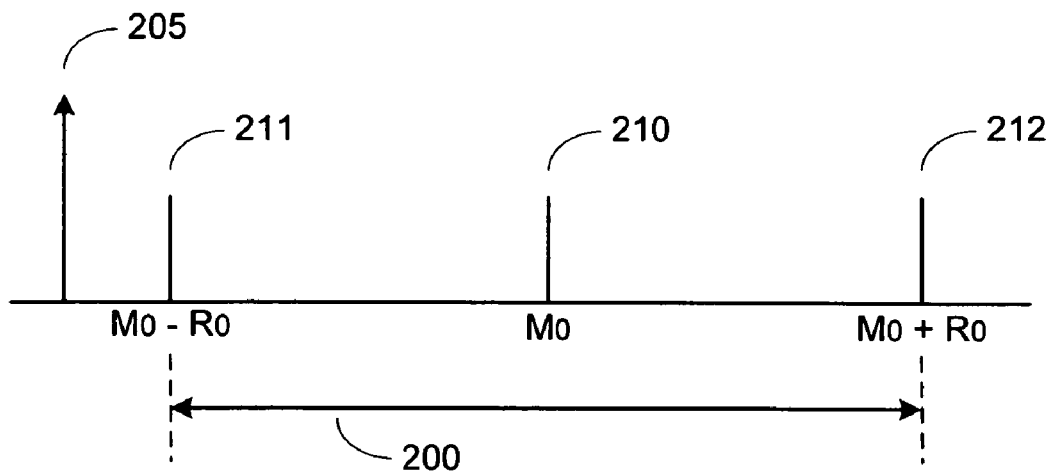
FIG. 2A illustrates an initialized cardiac response classification interval in accordance with embodiments of the invention.
Figure 2B:
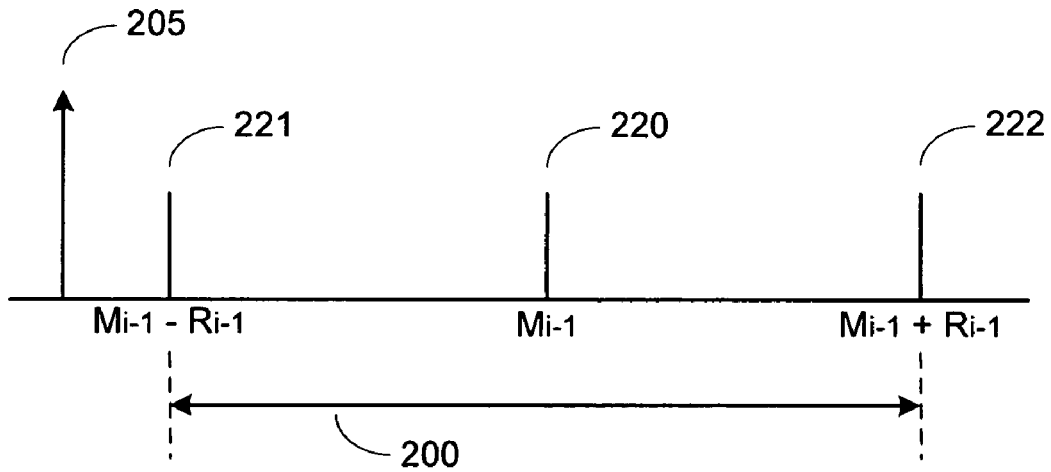
FIGS. 2B and 2C illustrate a cardiac response classification interval before and after adaptation, respectively, in accordance with embodiments of the invention.
Figure 2C:
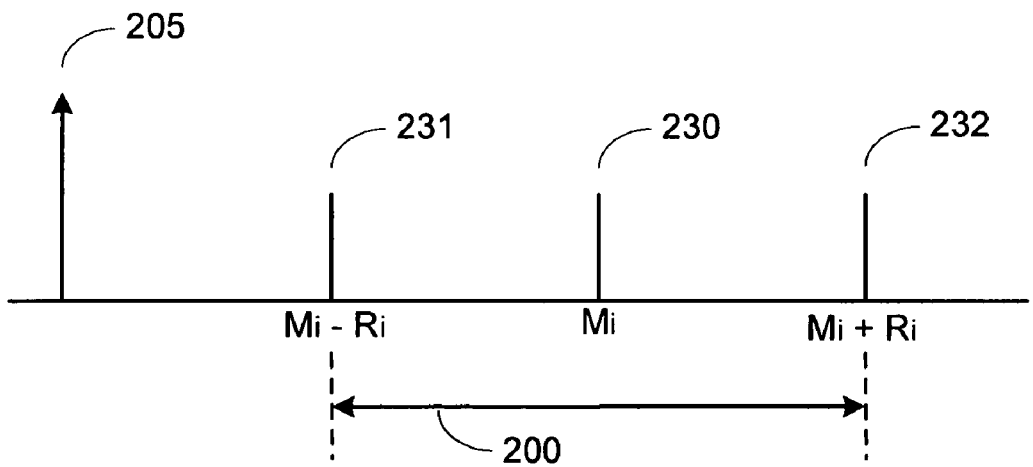

An embodiment of the invention involving an adaptable classification interval is illustrated in FIGS. 2A-2C. A captured response template comprising a peak amplitude and a peak amplitude timing, $T_0$, is acquired during an initialization process. The classification interval 200 is initialized as an interval of time following a pacing pulse 205. The initial cardiac response classification interval 200 uses $T_0$ as the initial center point 210, $M_0$, of the classification interval 200. A predetermined range, $R_0$, is selected and used as the initial range for the initial classification interval. Thus, the initial cardiac response classification interval has an initial midpoint 210, $M_0$, an upper range limit 212 of $M_0+R_0$, and a lower range limit 211 of $M_0-R_0$.

FIGS. 2B and 2C illustrate the adaptation of the classification interval. FIG. 2B illustrates the classification interval prior to adaptation. The center point 220 of the classification interval is designated $M_{i-1}$. The upper range limit 222 of the classification interval is designated $M_{i-1}+R_{i-1}$ and the lower range limit 221 is designated $M_{i-1}-R_{i-1}$. FIG. 2C illustrates the cardiac response classification interval after the next paced beat, referred to as the $i^{th}$ beat. The peak amplitude time, $T_i$, of the $i^{th}$ beat is determined. If $T_i$ falls into the range of $[M_{i-1}-R_{i-1}, M_{i-1}+R_{i-1}]$, then the $i^{th}$ beat is considered to be a non-fusion, captured beat and $T_i$ is used to adapt the classification interval. Otherwise, the $i^{th}$ beat is considered fusion and the range will not be updated using the information from that beat.

In one embodiment, $T_i$ is used to generate a new central point 230, $M_i$, a new lower range 231, $M_i-R_i$, and a new upper range 232, $M_i+R_i$, of an adapted classification interval as illustrated in FIG. 2C. A new value for $M_i$ may be determined, for example, based on a statistical function of the peak timing associated with the previous capture beats. In one example, a new value for $M_i$ comprises the average of the peak amplitude timing values of all the previous captured beats, $T_k$, where k=1, 2, 3, . . . , i. Other statistical functions (weighted average, median value) may alternatively be used to calculate $M_i$. A new value for $R_i$ may be calculated, for example, as f*SD, where f is a constant, and SD is the standard deviation of the peak amplitude timings of all previous captured beats, $T_k$.

Figure 3:
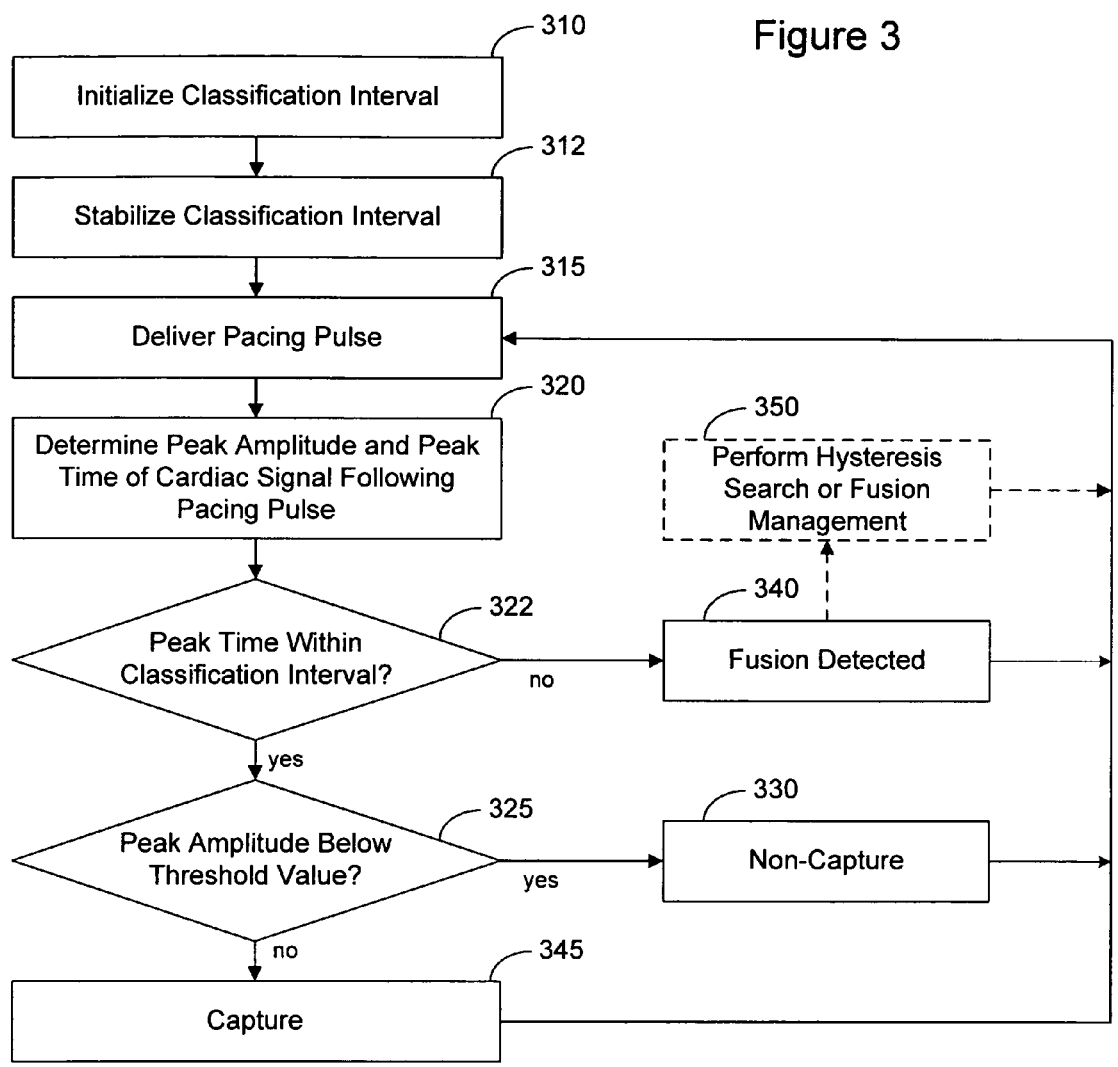
FIG. 3 is a flowchart illustrating a method of classifying a cardiac response to pacing using an adaptable classification interval in accordance with embodiments of the invention.

FIG. 3 is a flowchart illustrating a method of classifying a cardiac response to a pacing pulse using an adapted classification interval in accordance with embodiments of the invention. The classification interval is initialized 310 to an initial center point and range. The initial classification interval is adjusted 312 for stability. During the stabilization process, the cardiac response classification interval including, for example, the midpoint, upper bound, and/or lower bound of the classification interval is modified based on one or more captured beats. In one implementation, the classification interval may be adjusted using a predetermined number of captured beats. In another implementation, the classification interval may be adjusted until a predetermined stability criteria is achieved.

Following delivery 315 of a pacing pulse to a heart chamber, the peak amplitude and peak time of the cardiac signal sensed in the heart chamber is determined 320. If the peak time is beyond 322 the classification interval, the cardiac pacing response is classified 340 as fusion. If the peak time falls within the classification interval, then the cardiac signal amplitude is checked 325.

If the peak amplitude is greater than or equal to 325 the threshold value, then the cardiac pacing response is classified 345 as capture. If the peak amplitude is less than 325 the threshold value, then the cardiac pacing response is classified as non-capture 330.

If fusion is detected 340, then the system may optionally initiate 350 a [fusion/hysteresis] search, a process that involves lengthening a pacing interval to encourage intrinsic activity to occur before the next pacing (in the application of beat-to-beat capture verification) or shortening a pacing interval to promote the next pacing (in the application of threshold testing). For example, in AAI or VVI pacing, the pacing escape interval (A-A interval or V-V interval) for the next cardiac cycle after fusion is detected may be lengthened to allow intrinsic activity to occur. In DDD pacing, the atrioventricular delay may be lengthened after detecting fusion to promote intrinsic activity.

If fusion is detected 340, then the system may optionally initiate 350 a fusion management process. Fusion management may involve, for example, sensing prior to delivery of a pacing pulse and delaying the pace if the sensed amplitude exceeds a sensing level threshold. A rise in the amplitude of the cardiac signal may indicate the presence of intrinsic activity. If no intrinsic activity is detected, a backup pace is delivered, the backup pace having sufficient energy to assure capture. Methods and systems involving fusion management techniques, aspects of which may be incorporated in the embodiments described herein, are discussed in commonly owned U.S. Pat. No. 6,038,474, which is incorporated herein by reference.

Figure 4:
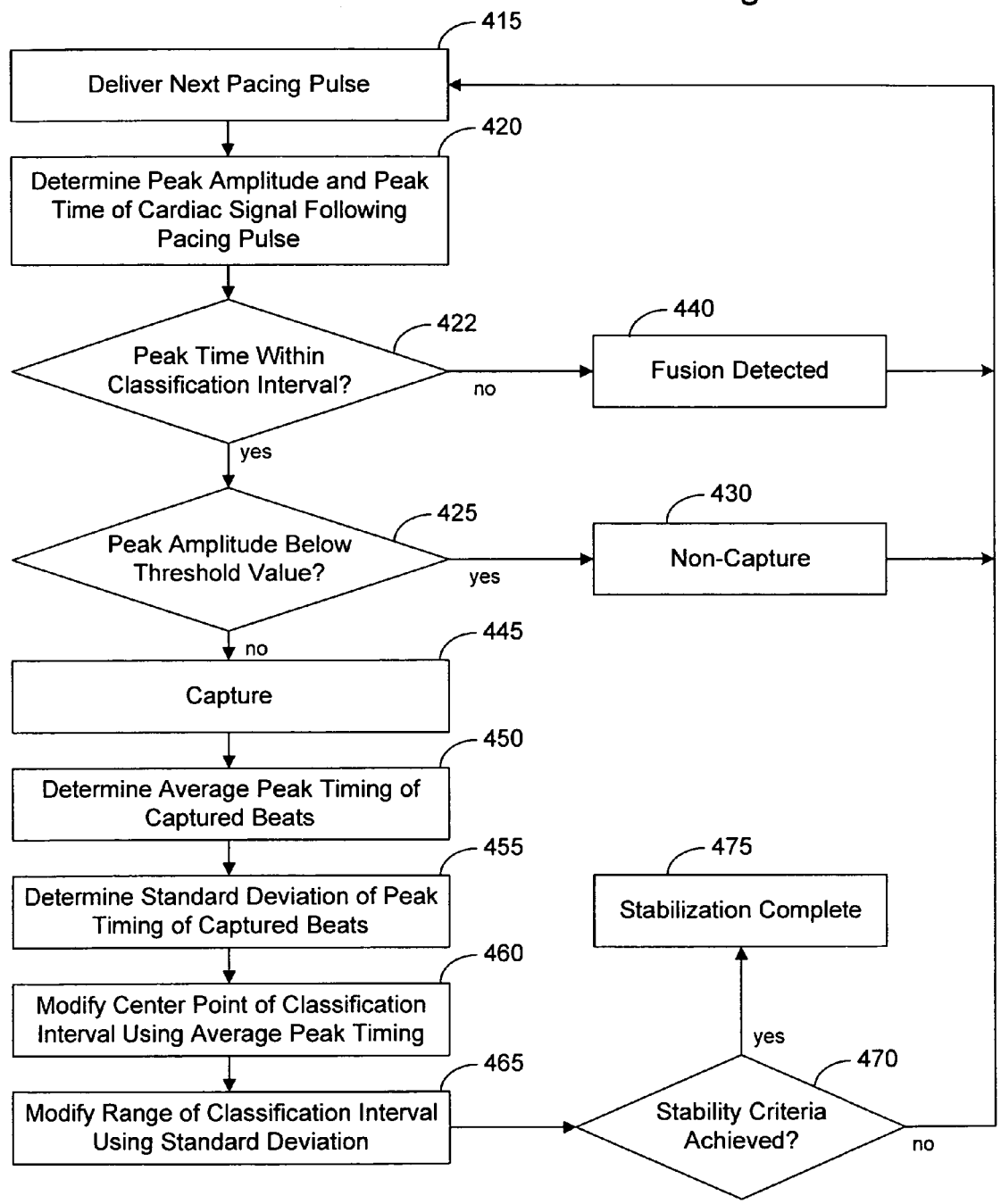
FIG. 4 is a flowchart illustrating a method of stabilizing a cardiac response classification interval in accordance with embodiments of the invention.

FIG. 4 is a flowchart illustrating a method of stabilizing the cardiac response classification interval that may be used, for example, at block 312 of FIG. 3. During this process, the cardiac response interval is adapted until stability is achieved. A pacing pulse is delivered 415 to the heart chamber. Following delivery 415 of the pacing pulse, the peak amplitude and peak timing of the cardiac signal sensed in the heart chamber are determined 420. If the peak time is beyond 422 the classification interval, the cardiac pacing response is classified 440 as fusion. If the peak time falls within 422 the classification interval, then the cardiac signal amplitude is checked 425.

If the peak amplitude is greater than or equal to 425 the threshold value, then the cardiac pacing response is classified 445 as capture. If the peak amplitude is less than 425 the threshold value, then the cardiac pacing response is classified 430 as non-capture.

If the cardiac response to pacing is classified 445 as capture, the peak timing of the cardiac signal is used to adapt the classification interval. The average and standard deviation of the peak timing of the captured beats is determined 450, 455. The center point of the classification interval is modified 460 using the average peak timing. The range of the classification interval is modified 465 using the standard deviation of the peak timing. If a predetermined stability criteria has been achieved 470, then stabilization is complete 475. Otherwise, the process continues until the stabilization criteria is met, or until the process times out. In one implementation, the stability criteria may involve, for example, the use of a predetermined number of beats to adapt the classification interval. In another implementation, adaptation of the classification interval may continue until a predetermined stability criteria is achieved, e.g., a variability of the center point and/or range below a predetermined value, such as if the standard deviation divided by the median value is below about 0.5.

By way of example, the processes of the present invention may be employed to determine the cardiac response in connection with threshold testing to determine the optimal energy for pacing. Determination of the optimal pacing energy may be implemented, for example, by a capture threshold testing procedure. Additionally, the cardiac response classification interval may be employed in connection with an automatic capture verification process used to monitor pacing responses on a beat-by-beat basis. Automatic capture verification may be used to control back up pacing when a pace pulse delivered to the heart fails to evoke a captured response (CR). These and other applications may be enhanced by employment of the systems and methods of the present invention.

Those skilled in the art will appreciate that reference to a capture threshold testing procedure indicates a method of determining the capture threshold in one of the left atrium, right atrium, left ventricle, and right ventricle. In such a procedure, the pacemaker, automatically or upon command, initiates a search for the capture threshold of the selected heart chamber. The capture threshold is defined as the lowest pacing energy that consistently captures the heart.

In one example of an automatic capture threshold procedure, the pacemaker delivers a sequence of pacing pulses to the heart and detects the cardiac responses to the pace pulses. The energy of the pacing pulses may be decreased in discrete steps until a predetermined number of loss-of-capture responses occur. The pacemaker may increase the stimulation energy in discrete steps until a predetermined number of capture responses occur to confirm the capture threshold. A capture threshold test may be performed using cardiac response classification methods of the present invention.

Other procedures for implementing capture threshold testing may be utilized. In one example, the pacing energy may be increased in discrete steps until capture is detected. In another example, the pacing energy may be adjusted according to a binomial search pattern.

Capture threshold determination is distinguishable from automatic capture detection, a procedure that typically occurs on a beat-by-beat basis during pacing. Automatic capture detection verifies that a delivered pace pulse results in a captured response. When a captured response is not detected following a pace pulse, the pacemaker may deliver a back up safety pace to ensure consistent pacing. The back up pace may be delivered, for example, about 70-80 ms after the initial pace pulse. If a predetermined number of pace pulses delivered during normal pacing do not produce a captured response, the pacemaker may initiate a capture threshold test to determine the capture threshold. Alternatively, if a predetermined number of pacing pulses do not produce a captured response, the pacemaker may adjust the pacing energy for the next pacing pulse. Automatic capture detection and back up pacing may be implemented using the adaptable classification intervals and/or the cardiac response classification processes of the present invention.

The pacing pulse may be delivered to any heart chamber and the cardiac response of the heart chamber to pacing may be determined by evaluating the cardiac signal sensed in the chamber following the pacing pulse. For example, the pacing stimulation may be delivered to one of the right ventricle, the left ventricle, the right atrium, and the left atrium. Various embodiments of the invention involve using the same electrode combination for pacing and sensing. Other embodiments involve using an electrode combination for pacing that is different from the electrode combination used to sense the cardiac signal following pacing. Employing different electrode combinations for pacing and sensing may enhance cardiac response classification. For example, using different electrode combinations for pacing and sensing may facilitate detection of capture, and/or may enhance discrimination between captured beats and fusion beats.

The embodiments described in connection with FIGS. 1-4 above involve the initialization and use of an adaptable classification interval. Other embodiments of the invention utilize a classification interval of a predetermined duration, and classify the cardiac pacing response based on the variability of one or more features of a cardiac signal detected within the classification interval. Selected features of the cardiac signal may be tracked beat-to-beat. The variability of the selected features may be used to discriminate between capture and fusion beats, for example.

Figure 5:
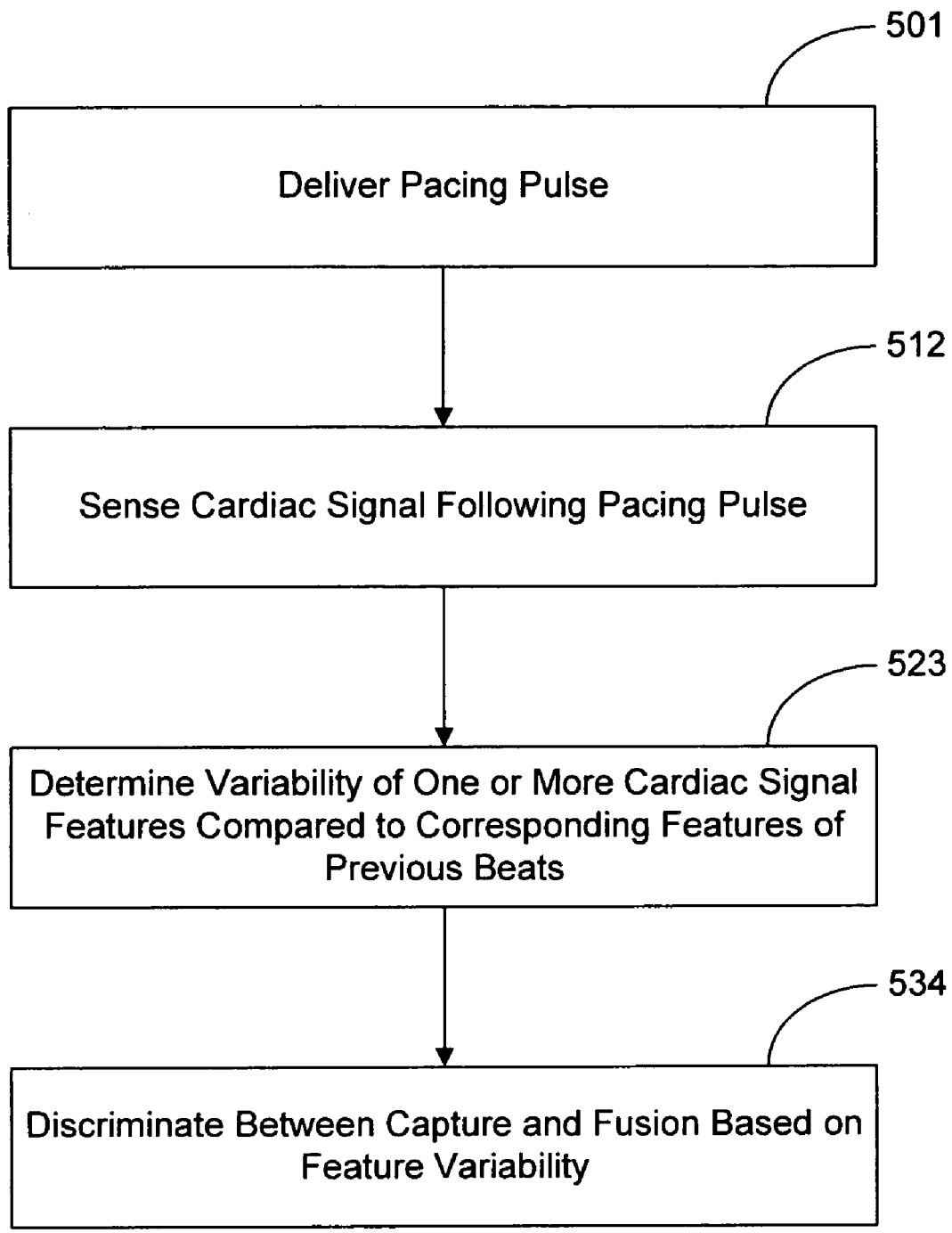
FIG. 5 is a flowchart illustrating a method of discriminating between capture and fusion based on the variability of a cardiac signal feature in accordance with embodiments of the invention.
Figure 6:
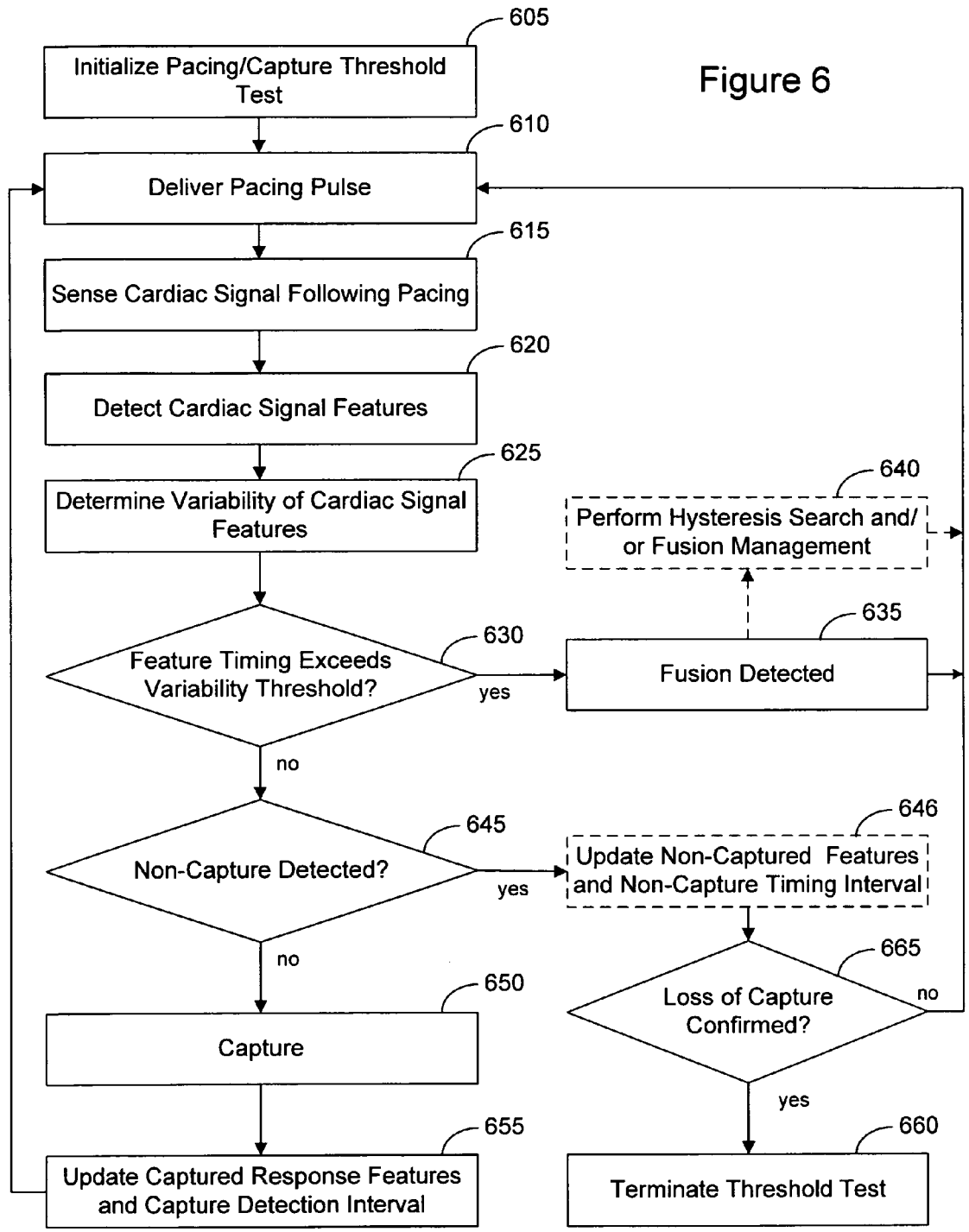
FIG. 6 is a flowchart illustrating a method of initiating a fusion search during a capture threshold test in accordance with embodiments of the invention.
Figure 7:
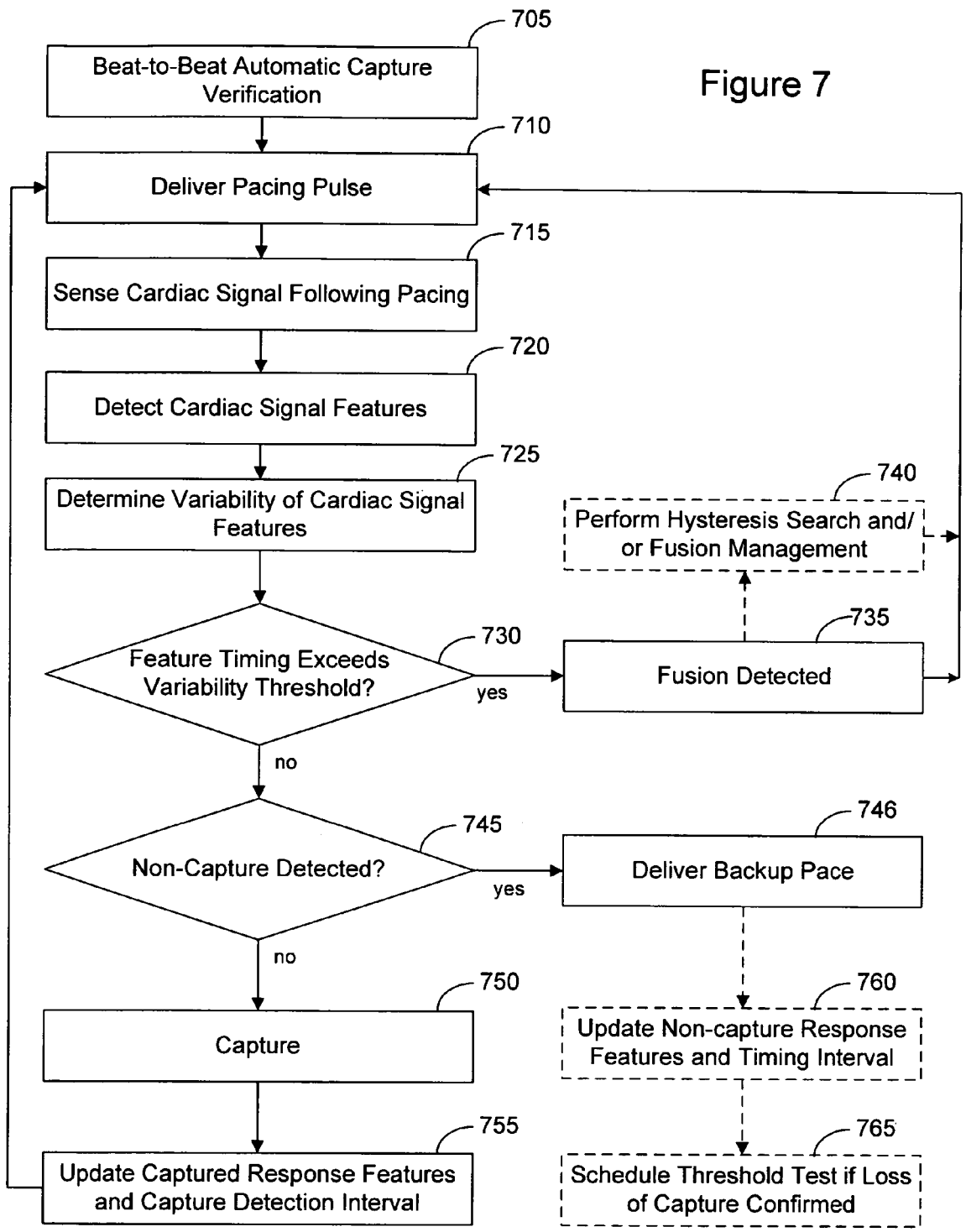
FIG. 7 is a flowchart illustrating a method of initiating a fusion search during beat-to-beat automatic capture verification in accordance with embodiments of the invention.

FIGS. 5, 6, and 7 illustrate capture detection methodologies based on the variability of selected features of the cardiac signal in accordance with embodiments of the invention. If the variability of selected features, such as peak amplitude or peak timing, are determined to be beyond a variability threshold, then the cardiac beat is classified as fusion. If the variability of the selected features are within the variability threshold, then the system may further classify the cardiac response, such as a captured beat or a non-captured beat. The variability threshold may be determined, for example, based on a standard deviation or other statistical function associated with a selected feature of previous cardiac signals representative of a particular type of cardiac response. The cardiac response classification methodologies illustrated in FIGS. 5, 6, and 7 are particularly useful in connection with discriminating between capture and fusion beats in either atrial or ventricular chambers.

The methodologies of the invention may be used in conjunction with pacing or capture threshold testing and/or with beat-to-beat automatic capture verification. FIG. 5 is a flowchart illustrating the process of discriminating between capture and fusion beats in accordance with embodiments of the invention. A pacing pulse is delivered 501 and the cardiac signal following the pacing pulse is sensed 512. One or more features of the cardiac signal are detected. The variability of the one or more features of the cardiac signal compared to the corresponding features of previous cardiac beats is determined 523. The system discriminates 534 between capture and fusion beats based on the variability of the cardiac signal features.

The flowchart of FIG. 6 further illustrates the process in details. During an initialization phase 605, the system delivers a series of pacing pulses and tracks the variability of cardiac signal features. A variability threshold for each tracked feature is determined based on the signals detected during the initialization phase.

Figure 8:
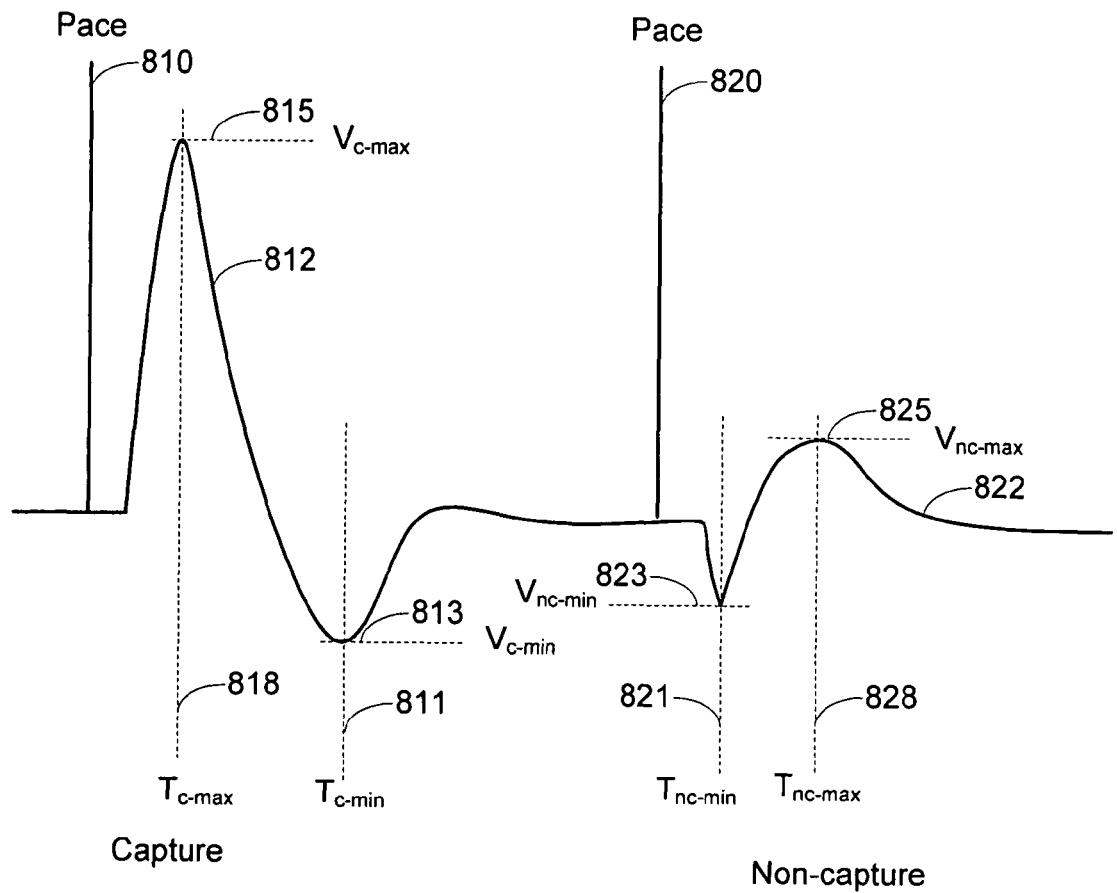
FIG. 8 is a graph illustrating cardiac signal features that may be utilized for discriminating between capture and fusion in accordance with embodiments of the invention.

A pacing pulse 610 is delivered to a heart chamber and the cardiac signal following the pacing pulse is sensed 615. The cardiac signal features of the cardiac signal are detected 620. For example, with reference to the graph of FIG. 8, if the cardiac signal is a non-captured signal 822, then the detected features of the cardiac signal may include one or more of the maximum peak amplitude 825, $V_{nc\text{-}max}$, the maximum peak amplitude timing 828, $T_{nc\text{-}max}$, the minimum peak amplitude 823, $V_{nc\text{-}min}$, and/or the minimum peak amplitude timing 821, $T_{nc\text{-}min}$.

If the cardiac signal is a captured response 812, then the detected features of the cardiac signal may include one or more of the maximum peak amplitude 815, $V_{c\text{-}max}$, the maximum peak amplitude timing 818, $T_{c\text{-}max}$, the minimum peak amplitude 813, $V_{c\text{-}min}$, and/or the minimum peak amplitude timing 811, $T_{c\text{-}min}$.

The system determines 625 the variability of the detected cardiac signal features. If the feature timing variability exceeds 630 a variability threshold, then fusion is detected 635. In this scenario, a hysteresis search or fusion management process may be implemented 640 as described above with reference to FIG. 3.

If the feature timing variability does not exceed 630 the variability threshold, the system checks to determine whether or not the pacing pulse produced capture. If non-capture is determined 645, then the cardiac signal may be used to update 646 one or more variability thresholds respectively associated with features of the non-captured response. For example, the non-captured peak timing may be used to update a non-captured peak timing variability threshold. In another example, a non-captured peak amplitude may be used to update a non-captured amplitude variability threshold.

If the beat is determined 650 to be a captured beat, then the cardiac signal is used to update 655 the capture detection interval and/or one or more variability thresholds respectively associated with features of the captured response. For example, the captured response peak timing may be used to update the range and/or midpoint of the classification interval. The peak timing of the captured response signal may be used to update the captured response peak timing variability threshold. The peak amplitude of the captured response signal may be used to update a captured amplitude variability threshold.

If the beat is determined 645 to be a captured beat, then the cardiac signal is used to update 655 the capture detection interval and/or one or more variability thresholds respectively associated with features of the captured response. For example, the captured response peak timing may be used to update the range and/or midpoint of the classification interval. The peak timing of the capture response signal may be used to update the captured response peak timing variability threshold. The peak amplitude of the captured response signal may be used to update a captured amplitude variability threshold.

The flow chart of FIG. 7 illustrates a capture detection methodology used for beat-to-beat automatic capture verification 705 in accordance with embodiments of the invention. A pacing pulse 710 is delivered to the heart chamber and the cardiac signal following the pacing pulse is sensed 715. The cardiac signal features of the cardiac signal are detected 720. For example, with reference to the graph of FIG. 8, if the cardiac signal is a non-captured signal 822, then the detected features of the cardiac signal may include one or more of the maximum peak amplitude 825, $V_{nc\text{-}max}$, the maximum peak amplitude timing 828, $T_{nc\text{-}max}$, the minimum peak amplitude 823, $V_{nc\text{-}min}$, and/or the minimum peak amplitude timing 821, $T_{nc\text{-}min}$.

If the cardiac signal is a captured response 812, then the detected features of the cardiac signal may include one or more of the maximum peak amplitude 815, $V_{c\text{-}max}$, the maximum peak amplitude timing 818, $T_{c\text{-}max}$, the minimum peak amplitude 813, $V_{c\text{-}min}$, and/or the minimum peak amplitude timing 811, $T_{c\text{-}min}$.

The system determines 725 the variability of the detected cardiac signal features. If the feature timing variability exceeds 730 a variability threshold, then fusion is detected 735. In this scenario, a hysteresis search or fusion management process may be implemented 740 as previously described with reference to FIG. 3.

If the feature timing variability does not exceed 730 the variability threshold, the system checks to determine whether or not the pacing pulse produced capture. If non-capture is determined 745, then a backup pace is typically delivered 746 at an energy level that assures capture. The non-captured cardiac signal may be used to update 760 one or more variability thresholds respectively associated with features of the non-captured response. For example, the non-captured peak timing may be used to update a non-captured peak timing variability threshold. In another example, a non-captured peak amplitude may be used to update a non-captured amplitude variability threshold. If loss of capture is confirmed, then a capture threshold test may optionally be scheduled 765.

If the beat is determined 750 to be a captured beat, then the cardiac signal represents a captured response signal and is used to update 755 the capture detection interval and/or one or more variability thresholds respectively associated with features of the captured response. For example, the captured response peak timing may be used to update the range and/or midpoint of the classification interval. The peak timing of the captured response signal may be used to update the captured response peak timing variability threshold. The peak amplitude of the captured response signal may be used to update the captured amplitude variability threshold.

The embodiments of the present system illustrated herein are generally described as being implemented in an implantable cardiac pacemaker/defibrillator (PD) that may operate in numerous pacing modes known in the art. Various types of single and multiple chamber implantable cardiac defibrillators are known in the art and may be used in connection with methods for initializing and adapting cardiac response classification intervals in accordance with the present invention. Methods of the invention may also be implemented in a variety of implantable or patient-external cardiac rhythm management devices, including single or multiple chamber pacemakers, defibrillators, cardioverters, bi-ventricular pacemakers, and cardiac resynchronizers, for example.

Although the present system is described in conjunction with an implantable cardiac pacemaker/defibrillator having a microprocessor-based architecture, it will be understood that the implantable cardiac pacemaker/defibrillator (or other device) may be implemented in any logic-based integrated circuit architecture, if desired.

Figure 9:
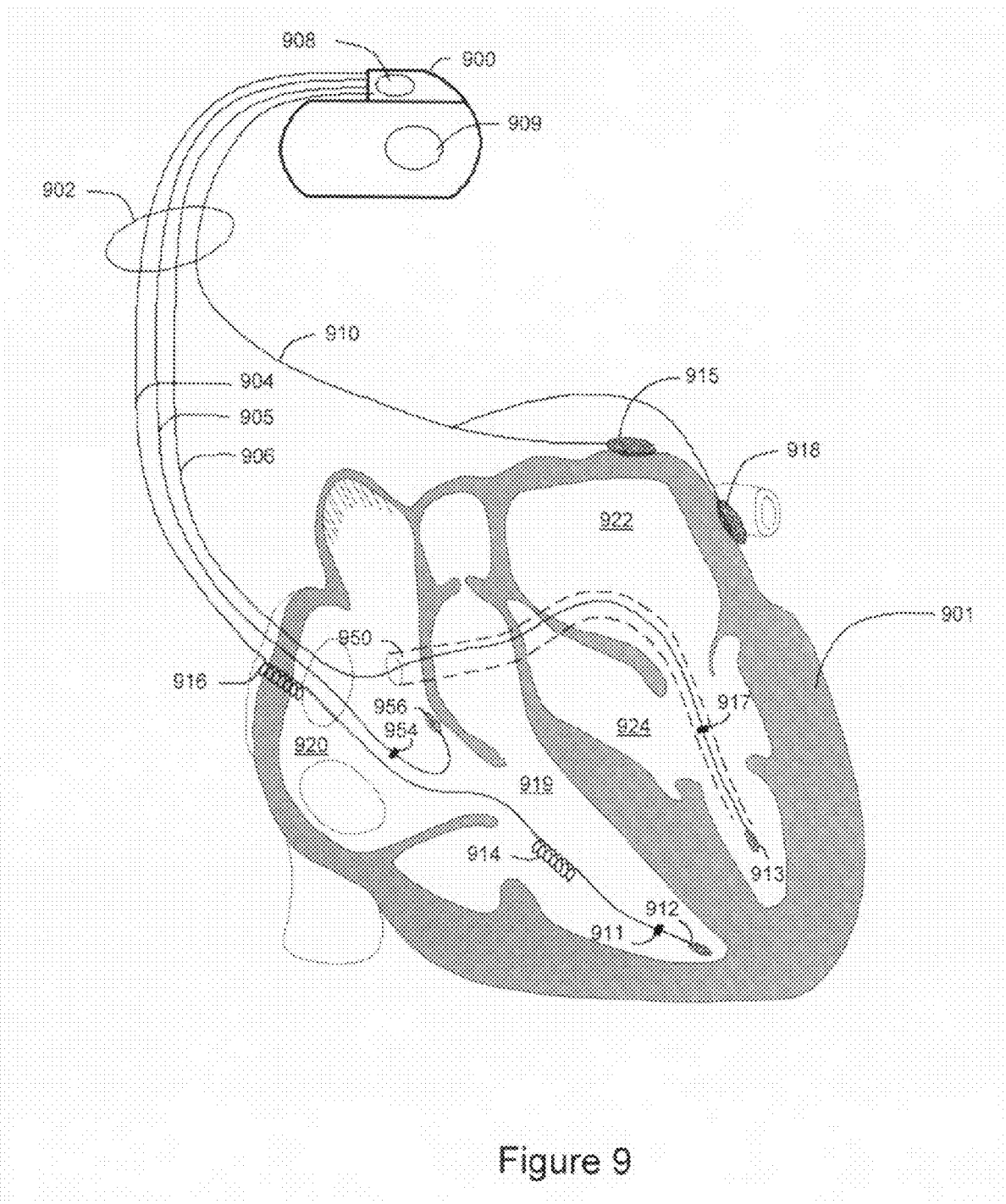
FIG. 9 is a partial view of one embodiment of an implantable medical device that may be used in connection with cardiac response classification in accordance with embodiments of the invention.

Referring now to FIG. 9 of the drawings, there is shown a cardiac rhythm management system that may be used to implement cardiac response classification interval determination of the present invention. The cardiac rhythm management (CRM) system in FIG. 9 includes a PD 900 electrically and physically coupled to a lead system 902. The housing and/or header of the PD 900 may incorporate one or more electrodes 908, 909 used to provide electrical stimulation energy to the heart and to sense cardiac electrical activity. The PD 900 may utilize all or a portion of the PD housing as a can electrode 909. The PD 900 may include an indifferent electrode 908 positioned, for example, on the header or the housing of the PD 900. If the PD 900 includes both a can electrode 909 and an indifferent electrode 908, the electrodes 908, 909 typically are electrically isolated from each other.

The lead system 902 is used to detect electric cardiac signals produced by the heart 901 and to provide electrical energy to the heart 901 under certain predetermined conditions to treat cardiac arrhythmias. The lead system 902 may include one or more electrodes used for pacing, sensing, and/or defibrillation. In the embodiment shown in FIG. 9, the lead system 902 includes an intracardiac right ventricular (RV) lead system 904, an intracardiac right atrial (RA) lead system 905, an intracardiac left ventricular (LV) lead system 906, and an extracardiac left atrial (LA) lead system 910. The lead system 902 of FIG. 9 illustrates one embodiment that may be used in connection with the methodologies described herein. Other leads and/or electrodes may additionally or alternatively be used.

The lead system 902 may include intracardiac leads 904, 905, 906 implanted in a human body with portions of the intracardiac leads 904, 905, 906 inserted into a heart 901. The intracardiac leads 904, 905, 906 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 9, the lead system 902 may include one or more extracardiac leads 910 having electrodes, e.g., epicardial electrodes, positioned at locations outside the heart for sensing and/or pacing one or more heart chambers.

The right ventricular lead system 904 illustrated in FIG. 9 includes an SVC-coil 916, an RV-coil 914, an RV-ring electrode 911, and an RV-tip electrode 912. The right ventricular lead system 904 extends through the right atrium 920 and into the right ventricle 919. In particular, the RV-tip electrode 912, RV-ring electrode 911, and RV-coil electrode 914 are positioned at appropriate locations within the right ventricle for sensing and delivering electrical stimulation pulses to the heart. The SVC-coil 916 is positioned at an appropriate location within the right atrium chamber of the heart 901 or a major vein leading to the right atrial chamber of the heart 901.

In one configuration, the RV-tip electrode 912 referenced to the can electrode 909 may be used to implement unipolar pacing and/or sensing in the right ventricle. Bipolar pacing and/or sensing in the right ventricle may be implemented using the RV-tip 912 and RV-ring 911 electrodes. In yet another configuration, the RV-ring 911 electrode may optionally be omitted, and bipolar pacing and/or sensing may be accomplished using the RV-tip electrode 912 and the RV-coil 914, for example. The right ventricular lead system 904 may be configured as an integrated bipolar pace/shock lead. The RV-coil 914 and the SVC-coil 916 are defibrillation electrodes.

The left ventricular lead 906 includes an LV distal electrode 913 and an LV proximal electrode 917 located at appropriate locations in or about the left ventricle for pacing and/or sensing the left ventricle. The left ventricular lead 906 may be guided into the right atrium of the heart via the superior vena cava. From the right atrium, the left ventricular lead 906 may be deployed into the coronary sinus ostium, the opening of the coronary sinus. The lead 906 may be guided through the coronary sinus to a coronary vein of the left ventricle. This vein is used as an access pathway for leads to reach the surfaces of the left ventricle that are not directly accessible from the right side of the heart. Lead placement for the left ventricular lead 906 may be achieved via subclavian vein access and a preformed guiding catheter for insertion of the LV electrodes 913, 917 adjacent to the left ventricle.

Unipolar pacing and/or sensing in the left ventricle may be implemented, for example, using the LV distal electrode 913 referenced to the can electrode 909. The LV distal electrode 913 and the LV proximal electrode 917 may be used together as bipolar sense and/or pace electrodes for the left ventricle. The left ventricular lead 906 and the right ventricular lead 904, in conjunction with the PD 900, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 905 includes an RA-tip electrode 956 and an RA-ring electrode 954 positioned at appropriate locations in the right atrium for sensing and pacing the right atrium. In one configuration, the RA-tip 956 referenced to the can electrode 909, for example, may be used to provide unipolar pacing and/or sensing in the right atrium 920. In another configuration, the RA-tip electrode 956 and the RA-ring electrode 954 may be used to effect bipolar pacing and/or sensing.

FIG. 9 illustrates one embodiment of a left atrial lead system 910. In this example, the left atrial lead 910 is implemented as an extracardiac lead with an LA distal electrode 918 and an LA proximal electrode 915 positioned at appropriate locations outside the heart 901 for sensing and pacing the left atrium. Unipolar pacing and/or sensing of the left atrium may be accomplished, for example, using the LA distal electrode 918 to the can 909 pacing vector. Bipolar pacing and/or sensing of the left atrium may be accomplished through the use of the LA distal electrode 918 and the LA proximal electrode 915.

Figure 10:
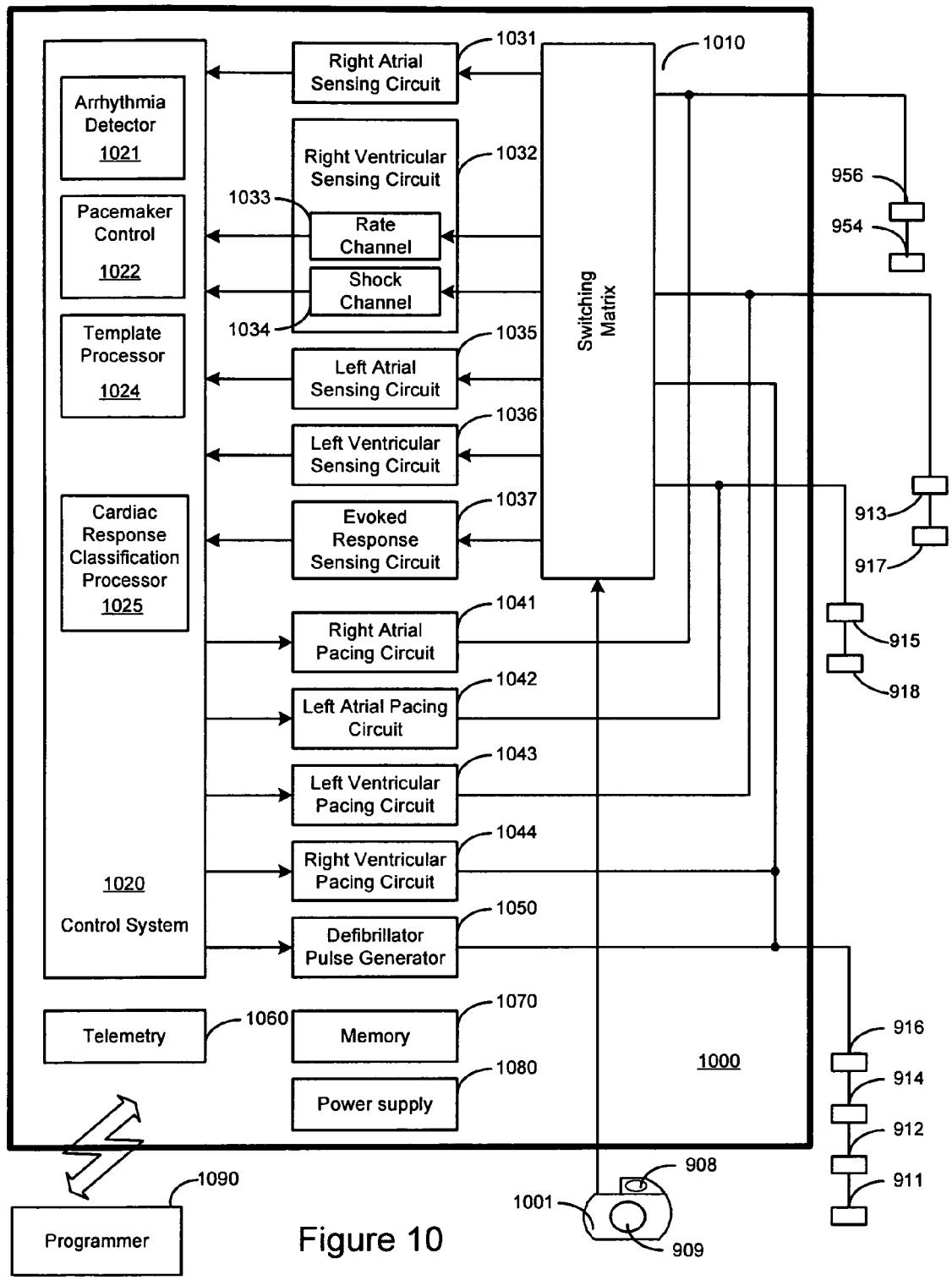
FIG. 10 is a block diagram of an implantable medical device that may be used to adapt a cardiac response classification interval and classify a cardiac response to pacing in accordance with embodiments of the invention.

Referring now to FIG. 10, there is shown an embodiment of a cardiac pacemaker/defibrillator 1000 suitable for implementing an atrial capture verification and retrograde management methodologies of the present invention. FIG. 10 shows a cardiac pacemaker/defibrillator divided into functional blocks. It is understood by those skilled in the art that there exist many possible configurations in which these functional blocks can be arranged. The example depicted in FIG. 10 is one possible functional arrangement. Other arrangements are also possible. For example, more, fewer, or different functional blocks may be used to describe a cardiac pacemaker/defibrillator suitable for implementing the methodologies of the present invention. In addition, although the cardiac pacemaker/defibrillator 1000 depicted in FIG. 10 contemplates the use of a programmable microprocessor-based logic circuit, other circuit implementations may be utilized.

The cardiac pacemaker/defibrillator 1000 depicted in FIG. 10 includes circuitry for receiving cardiac signals from a heart and delivering electrical stimulation energy to the heart in the form of pacing pulses or defibrillation shocks. In one embodiment, the circuitry of the cardiac pacemaker/defibrillator 1000 is encased and hermetically sealed in a housing 1001 suitable for implanting in a human body. Power to the cardiac pacemaker/defibrillator 1000 is supplied by an electrochemical battery 1080. A connector block (not shown) is attached to the housing 1001 of the cardiac pacemaker/defibrillator 1000 to allow for the physical and electrical attachment of the lead system conductors to the circuitry of the cardiac pacemaker/defibrillator 1000.

The cardiac pacemaker/defibrillator 1000 may be a programmable microprocessor-based system, including a control system 1020 and a memory 1070. The memory 1070 may store parameters for various pacing, defibrillation, and sensing modes, along with other parameters. Further, the memory 1070 may store data indicative of cardiac signals received by other components of the cardiac pacemaker/defibrillator 1000. The memory 1070 may be used, for example, for storing historical EGM and therapy data. The historical data storage may include, for example, data obtained from long term patient monitoring used for trending or other diagnostic purposes. Historical data, as well as other information, may be transmitted to an external programmer unit 1090 as needed or desired.

The control system 1020 may cooperate with other components of the cardiac pacemaker/defibrillator 1000 to control the operations of the cardiac pacemaker/defibrillator 1000. In one example, the cardiac pacemaker/defibrillator 1000 may incorporate a sensor for determining the patient's hemodynamic need. The sensor output may be utilized by the control system 1020 to deliver pacing at a rate adapted to the activity level of the patient. In some implementations, the cardiac pacemaker/defibrillator 1000 may include components of an accelerometer and/or a transthoracic impedance sensor for determining the activity level and/or respiration rate of the patient.

The control system 1020 depicted in FIG. 10 incorporates a cardiac response classification processor 1025 for determining cardiac responses to pacing stimulation in accordance with various embodiments of the present invention. The control system 1020 may include additional functional components including a pacemaker control circuit 1022, an arrhythmia detector 1021, and a template processor 1024, along with other components for controlling the operations of the cardiac pacemaker/defibrillator 1000.

Telemetry circuitry 1060 may be implemented to provide communications between the cardiac pacemaker/defibrillator 1000 and an external programmer unit 1090. In one embodiment, the telemetry circuitry 1060 and the programmer unit 1090 communicate using a wire loop antenna and a radio frequency telemetric link, as is known in the art, to receive and transmit signals and data between the programmer unit 1090 and the telemetry circuitry 1060. In this manner, programming commands and other information may be transferred to the control system 1020 of the cardiac pacemaker/defibrillator 1000 from the programmer unit 1090 during and after implant. In addition, stored cardiac data pertaining to capture threshold, capture detection, and/or cardiac response classification, for example, along with other data, may be transferred to the programmer unit 1090 from the cardiac pacemaker/defibrillator 1000.

In the embodiment of the cardiac pacemaker/defibrillator 1000 illustrated in FIG. 10, electrodes RA-tip 956, RA-ring 954, RV-tip 912, RV-ring 911, RV-coil 914, SVC-coil 916, LV distal electrode 913, LV proximal electrode 917, LA distal electrode 918, LA proximal electrode 915, indifferent electrode 908, and can electrode 909 are coupled through a switch matrix 1010 to sensing circuits 1031-1037.

A right atrial sensing circuit 1031 serves to detect and amplify electrical signals from the right atrium of the heart. Unipolar sensing may be implemented, for example, by sensing voltages developed between the RA-tip 956 and the can electrode 909. Outputs from the right atrial sensing circuit are coupled to the control system 1020.

A right ventricular sensing circuit 1032 serves to detect and amplify electrical signals from the right ventricle of the heart. Right ventricular cardiac signals sensed through use of the RV-tip 912 electrode are right ventricular near-field signals and are denoted RV rate channel signals. A bipolar RV rate channel signal may be sensed as a voltage developed between the RV-tip 912 and the RV-ring 911. Alternatively, bipolar sensing in the right ventricle may be implemented using the RV-tip electrode 912 and the RV-coil 914. Unipolar rate channel sensing in the right ventricle may be implemented, for example, by sensing voltages developed between the RV-tip 912 and the can electrode 909.

Right ventricular cardiac signals sensed through use of defibrillation electrodes are far-field signals, also referred to as RV morphology or RV shock channel signals. More particularly, a right ventricular shock channel signal may be detected as a voltage developed between the RV-coil 914 and the SVC-coil 916. A right ventricular shock channel signal may also be detected as a voltage developed between the RV-coil 914 and the can electrode 909. In another configuration, the can electrode 909 and the SVC-coil electrode 916 may be electrically shorted and an RV shock channel signal may be detected as the voltage developed between the RV-coil 914 and the can electrode 909/SVC-coil 916 combination.

Left atrial cardiac signals may be sensed through the use of one or more left atrial electrodes 915, 918, which may be configured as epicardial electrodes. A left atrial sensing circuit 1035 serves to detect and amplify electrical signals from the left atrium of the heart. Bipolar sensing and/or pacing in the left atrium may be implemented, for example, using the LA distal electrode 918 and the LA proximal electrode 915. Unipolar sensing and/or pacing of the left atrium may be accomplished, for example, using the vector from the LA distal electrode 918 to the can electrode 909 or the LA proximal electrode 915 to the can electrode 909.

A left ventricular sensing circuit 1036 serves to detect and amplify electrical signals from the left ventricle of the heart. Bipolar sensing in the left ventricle may be implemented, for example, by sensing voltages developed between the LV distal electrode 913 and the LV proximal electrode 917. Unipolar sensing may be implemented, for example, by sensing voltages developed between the LV distal electrode 913 or the LV proximal electrode 917 to the can electrode 909.

Optionally, an LV coil electrode (not shown) may be inserted into the patient's cardiac vasculature, e.g., the coronary sinus, adjacent to the left heart. Signals detected using combinations of the LV electrodes 913, 917, LV coil electrode (not shown), and/or the can electrode 909 may be sensed and amplified by the left ventricular sensing circuitry 1036. The output of the left ventricular sensing circuit 1036 is coupled to the control system 1020.

The outputs of the switching matrix 1010 may be operated to couple selected combinations of electrodes 911, 912, 913, 914, 916, 917, 918, 954, and 956 to an evoked response sensing circuit 1037. The evoked response sensing circuit 1037 serves to sense and amplify voltages developed using various combinations of electrodes for cardiac response classification in accordance with embodiments of the invention.

In the embodiments described below, various combinations of pacing and sensing electrodes may be utilized in connection with pacing and sensing the cardiac signal following the pace pulse to classify the cardiac response to the pacing pulse. For example, in some embodiments, a first electrode combination is used for pacing a heart chamber and a second electrode combination is used to sense the cardiac signal following pacing. In other embodiments, the same electrode combination is used for pacing and sensing. Further, the electrodes used to sense for the retrograde P-wave may be different or the same as the electrodes used to sense for the atrial evoked response.

The pacemaker control circuit 1022, in combination with pacing circuitry for the left atrium, right atrium, left ventricle, and right ventricle may be implemented to selectively generate and deliver pacing pulses to the heart using various electrode combinations. The pacing electrode combinations may be used to effect bipolar or unipolar pacing of the heart chambers as described above.

As described above, bipolar or unipolar pacing pulses may be delivered to a heart chamber using one of the pacing vectors as described above. The electrical signal following the delivery of the pacing pulses may be sensed through various sensing vectors coupled through the switch matrix 1010 to the cardiac response classification processor 1025 and used to classify the cardiac response to pacing.

The switching matrix 1010 may be arranged to provide connections to various configurations of pacing and defibrillation electrodes. The outputs of the switching matrix 1010 may be coupled to an evoked response (ER) sensing circuit 1037 that serves to sense and amplify cardiac signals detected between the selected combinations of electrodes. The detected signals are coupled through the ER amplifier 1037 to a cardiac response classification processor 1025. The cardiac response classification processor 1025 includes circuitry configured to determine the cardiac response to a pacing stimulation. The presence or absence of an evoked response may be determined based on the amplitude, peak value, peak timing, and/or other morphological features of the cardiac signal sensed following the pacing pulse in accordance with embodiments of the invention.

The cardiac response classification methods described herein involve an adaptable classification interval that may be particularly useful in discriminating captured responses from fusion beats. Fusion management is important in automatic capture verification. Further, erroneous classification of cardiac responses to pacing in capture threshold testing may produce either an underestimation or overestimation of the capture threshold. Erroneous classification of cardiac responses to pacing may result in the pacing energy being set too high or too low resulting in an incorrect determination of the optimal pacing energy. The use of an adaptable classification interval rather than a fixed interval provides a classification interval that is adapted for each individual, thus providing more effective fusion management. Various methods and systems for initializing and adapting templates and/or classification intervals useful for capture threshold testing and capture verification, aspects of which may be utilized in connection with implementing an adaptable cardiac response classification interval according to embodiments of the invention, are described in commonly owned U.S. patent application Ser. No. 10/448,260, filed May 28, 2003, now U.S. Patent Publication 20040243014, which is incorporated herein by reference.

A number of the examples presented herein involve block diagrams illustrating functional blocks used for coordinated monitoring, diagnosis, and/or therapy functions in accordance with embodiments of the present invention. It will be understood by those skilled in the art that there exist many possible configurations in which these functional blocks can be arranged and implemented. The examples depicted herein provide examples of possible functional arrangements used to implement the approaches of the invention.

It is understood that the components and functionality depicted in the figures and described herein can be implemented in hardware, software, or a combination of hardware and software. It is further understood that the components and functionality depicted as separate or discrete blocks/elements in the figures in general can be implemented in combination with other components and functionality, and that the depiction of such components and functionality in individual or integral form is for purposes of clarity of explanation, and not of limitation.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of operating a cardiac medical device to automatically form a cardiac response classification interval during which a cardiac signal is sensed to determine a cardiac response of a heart to pacing, the method comprising:
   sensing one or more cardiac signals associated with a type of cardiac pacing response;
   determining timing variability of one or more features of the cardiac signals;
   forming the cardiac response classification interval including temporally orienting the classification interval with respect to timing of the one or more cardiac signal features, and setting a duration of the classification interval using the timing variability of the one or more cardiac signal features;
   determining the cardiac response to pacing using the classification interval;
   delivering pacing therapy to the heart based on determination of the cardiac pacing response; and
   determining whether a predetermined stability criterion has been achieved based on the variability of a parameter of the cardiac response classification interval being below a predetermined value;

wherein forming the cardiac response classification interval comprises adapting an upper or lower bound of the classification interval until the predetermined stability criterion is determined to be achieved.

2. The method of claim 1, wherein the one or more features comprises a peak amplitude.

3. The method of claim 1, wherein the type of cardiac pacing response comprises a captured response.

4. The method of claim 1, wherein determining the timing variability comprises determining a standard deviation.

5. The method of claim 1, further comprising adapting the cardiac response classification interval using one or more additional cardiac signals.

6. The method of claim 1, wherein forming the cardiac response classification interval comprises:
   determining values for the timing of a particular feature for each of the cardiac signals;
   averaging the particular feature timing values;
   determining a standard deviation of the particular feature timing values;
   using the average feature timing value as a central point;
   defining a timing interval around the central point using the standard deviation; and
   forming the cardiac response classification interval based on the timing interval.

7. The method of claim 1, further comprising using the classification interval to determine a captured response to a pacing pulse.

8. The method of claim 1, further comprising using the classification interval to discriminate between a captured or non-captured response and a fusion beat.

9. The method of claim 1, wherein forming the cardiac response classification interval comprises adapting the upper or lower bound of the classification interval based on a predetermined number of cardiac beats.

10. A medical system, comprising:
    a pacing circuit configured to deliver pacing pulses to a heart chamber;
    a sensing circuit configured to sense cardiac signals associated with the pacing pulses;
    a processor coupled to the sensing circuit, the processor configured to determine a cardiac response classification interval defining a period of time after a pacing pulse that a cardiac signal is sensed to determine a response to the pacing pulse, the processor configured to temporally orient the classification interval with respect to timing of at least one cardiac signal feature, and to determine a duration of the classification interval based on a timing variability of the at least one cardiac signal feature, the cardiac signal feature associated with a type of cardiac pacing response; and
    cardiac response classification circuitry configured to determine a cardiac response to pacing using the classification interval, wherein the pacing circuit is configured to deliver pacing therapy based at least in part on determination of the cardiac pacing response;
    wherein the processor is further configured to determine the variability of a parameter of the cardiac response classification interval, determine whether a predetermined stability criterion has been achieved based on the variability of the parameter of the cardiac response classification interval being below a predetermined value, and adapt the cardiac response classification interval until the stability criterion is determined to be achieved.

11. The system of claim 10, wherein the feature comprises a peak amplitude.

12. The system of claim 10, wherein the type of cardiac pacing response comprises a captured response.

13. The system of claim 10, wherein the processor is configured to determine the standard deviation of the feature timing.

14. The system of claim 10, wherein the processor is configured to determine values for the timing of the feature for each of the cardiac signals, average the feature timing values, determine a standard deviation of the feature timing values, and form the cardiac response classification interval based on the average feature timing and the standard deviation.

15. A system for forming a cardiac response classification interval used for sensing a cardiac signal following a pacing pulse to determine a response to the pacing pulse, comprising:
    means for sensing cardiac signals associated with a type of cardiac pacing response;
    means for determining a variability of a timing of one or more features of the cardiac signals;
    means for forming the cardiac response classification interval including temporally orienting the classification interval with respect to the timing of the one or more features, and setting a duration of the classification interval using the timing variability;
    means for determining a cardiac pacing response using the cardiac response classification interval;
    pacing circuitry configured to deliver pacing therapy based at least in part on determination of the cardiac pacing response; and
    means for determining whether a predetermined stability criterion has been achieved based on comparison of a predetermined value to the variability of a parameter of the cardiac response classification interval;
    wherein the forming means also adapts an upper or lower bound of the classification interval until the predetermined stability criterion is determined to be achieved.

16. The system of claim 15, wherein the means for forming the cardiac response classification interval is configured to modify the cardiac response classification interval using one or more additional cardiac signals sensed during delivery of a pacing therapy.

17. The system of claim 15, wherein the means for determining the cardiac pacing response is configured to detect capture using the cardiac response classification interval.

18. The method of claim 1, further comprising determining peak amplitude and peak time of a cardiac signal associated with delivery of a pacing pulse, wherein determining the cardiac response to pacing using the classification interval comprises discriminating between capture, non-captured, and fusion responses to the pacing pulse, wherein:
    the response is indicated as fusion if the peak time is not within the classification interval;
    the response is indicated as non-capture if the peak time is within the classification interval and the peak amplitude is below a threshold; and
    the response is indicated as capture if the peak time is within the classification interval and the peak amplitude is above the threshold.

19. The system of claim 10, wherein the cardiac response classification circuitry is configured to determine peak amplitude and peak time of a cardiac signal that is associated with delivery of a pacing pulse and to determine the cardiac response using the classification interval by discriminating between capture, non-captured, and fusion responses to the pacing pulse, wherein:

the response is indicated as fusion if the peak time is not within the classification interval;

the response is indicated as non-capture if the peak time is within the classification interval and the peak amplitude is below a threshold; and the response is indicated as capture if the peak time is within the classification interval and the peak amplitude is above the threshold.

* * * * *